(12) United States Patent
Murray et al.

(10) Patent No.: US 7,348,465 B2
(45) Date of Patent: Mar. 25, 2008

(54) SELECTIVE ALKYLATION OF AROMATIC HYDROCARBONS

(75) Inventors: Brendan Dermot Murray, Houston, TX (US); Narayana Mysore, Houston, TX (US); James William Yaeger, Katy, TX (US)

(73) Assignee: Shell Oil Company, Houston, TX (US)

( * ) Notice: Subject to any disclaimer, the term of this patent is extended or adjusted under 35 U.S.C. 154(b) by 641 days.

(21) Appl. No.: 11/053,559

(22) Filed: Feb. 8, 2005

(65) Prior Publication Data
US 2006/0178544 A1    Aug. 10, 2006

(51) Int. Cl.
C07C 2/68    (2006.01)
(52) U.S. Cl. ...................................................... 585/467
(58) Field of Classification Search ................ 585/467
See application file for complete search history.

(56) References Cited

U.S. PATENT DOCUMENTS

| | | | |
|---|---|---|---|
| 3,308,069 A | 3/1967 | Wadlinger et al. | |
| RE28,341 E | 2/1975 | Wadlinger et al. | |
| 4,301,316 A | 11/1981 | Young | |
| 4,329,509 A | 5/1982 | Haag et al. | |
| 4,508,837 A | 4/1985 | Zones | |
| 4,570,027 A | 2/1986 | Boucher et al. | |
| 4,849,569 A | 7/1989 | Smith, Jr. | |
| 4,876,408 A | 10/1989 | Ratcliffe et al. | |
| 4,891,458 A | 1/1990 | Innes et al. | |
| 4,950,834 A | 8/1990 | Arganbright et al. | |
| 4,954,325 A | 9/1990 | Rubin et al. | |
| 4,978,807 A | 12/1990 | Smith, Jr. | |
| 5,081,323 A | 1/1992 | Innes et al. | |
| 5,082,990 A | 1/1992 | Hsieh et al. | |
| 5,120,403 A | 6/1992 | Smith, Jr. | |
| 5,149,894 A | 9/1992 | Holtermann ................ 585/467 |
| 5,176,883 A | 1/1993 | Smith, Jr. et al. | |
| 5,191,136 A | 3/1993 | Takahashi et al. | |
| 5,204,064 A | 4/1993 | Smith, Jr. | |
| 5,221,441 A | 6/1993 | Smith, Jr. | |
| 5,258,570 A | 11/1993 | Skeels et al. | |
| 5,262,576 A | 11/1993 | Smith, Jr. | |

(Continued)

FOREIGN PATENT DOCUMENTS

EP         55046         6/1982

(Continued)

OTHER PUBLICATIONS

Meyers, Robert A., Handbook of Petroleum Refining Processes, McGraw Hill (3rd Ed. 2004), entire book, particularly 2.3-2.11, 2.13-2.23, 2.25-2.26, 4.3-4.31.

(Continued)

*Primary Examiner*—Thuan Dinh Dang

(57) ABSTRACT

A method for increasing selectivity of alkylation to monoalkylation comprising: providing a feedstream consisting essentially of alkylating agent and a stoichiometric excess of benzene, the alkylating agent consisting essentially of a molar blend of propylene and one or more linear butene(s); and, contacting the feedstream with a catalytically effective amount of zeolite beta under alkylation reaction conditions which increase selectivity of the alkylation to monoalkylation compared to predicted selectivity to monoalkylation based on the concentration of the alkylating agent and on the molar blend of propylene and one or more linear butene(s).

33 Claims, 9 Drawing Sheets

U.S. PATENT DOCUMENTS

| | | |
|---|---|---|
| 5,298,667 A | 3/1994 | Iwanaga et al. |
| 5,304,684 A | 4/1994 | Nishida et al. |
| 5,345,006 A | 9/1994 | Smith, Jr. |
| 5,723,710 A | 3/1998 | Gajda et al. |
| 5,756,872 A | 5/1998 | Smith, Jr. et al. ........... 585/449 |
| 5,894,076 A | 4/1999 | Hearn et al. ................. 585/251 |
| 2002/0038067 A1 | 3/2002 | Dandekar et al. |
| 2002/0111522 A1 | 8/2002 | Overbeek et al. |
| 2002/0137977 A1 | 9/2002 | Hendriksen |

FOREIGN PATENT DOCUMENTS

| | | |
|---|---|---|
| EP | 64328 | 11/1982 |
| EP | 95304 | 11/1983 |
| EP | 159846 | 10/1985 |
| EP | 159847 | 10/1985 |
| EP | 164939 | 12/1985 |
| EP | 439 632 A1 | 8/1991 |
| GB | 2024790 | 1/1980 |
| WO | WO 98/09928 | 3/1998 |

OTHER PUBLICATIONS

International Search Report for PCT/US2006/004235 (TH2317 PCT) dated Jun. 13, 2006.

SELECTIVE ALKYLATION OF AROMATIC HYDROCARBONS

FIELD OF THE INVENTION

The present application relates to methods for increasing selectivity during alkylation of aromatic hydrocarbons.

BACKGROUND OF THE INVENTION

Methods are needed for enhancing selectivity of aromatic alkylation to monoalkylated species.

SUMMARY OF THE INVENTION

The application provides a method for increasing selectivity of aromatic alkylation to monoalkylation. The method comprises: providing a feedstream consisting essentially of alkylating agent and a stoichiometric excess of benzene, the alkylating agent consisting essentially of a molar blend of propylene and one or more linear butene(s); and, contacting the feedstream with a catalytically effective amount of zeolite beta under alkylation reaction conditions which increases selectivity of the alkylation to monoalkylation compared to predicted selectivity to monoalkylation based on the concentration of the alkylating agent and on the molar blend of propylene and one or more linear butene(s).

DETAILED DESCRIPTION

Cumene and s-butyl benzene are used as feedstocks to produce phenol. Cumene and s-butylbenzene generally are produced by alkylating benzene. Typical alkylation processes produce di- and/or tri-alkylated products along with the desired monoalkylated products, cumene and s-butylbenzene. Phenol production is more efficient using substantially pure feedstocks of cumene/s-butyl benzene. The di- and/or tri-alkylated products generally must be removed and/or converted to monoalkylated product in a transalkylator before using the cumene or s-butylbenzene as a feed to produce phenol.

The present application is directed to a method for increasing selectivity of aromatic alkylation to monoalkylation. The method uses zeolite beta as the alkylation catalyst, and uses an alkylation agent consisting essentially of a molar blend of propylene and one or more linear butene(s).

The Surprising Increase in Selectivity

Figure 1:
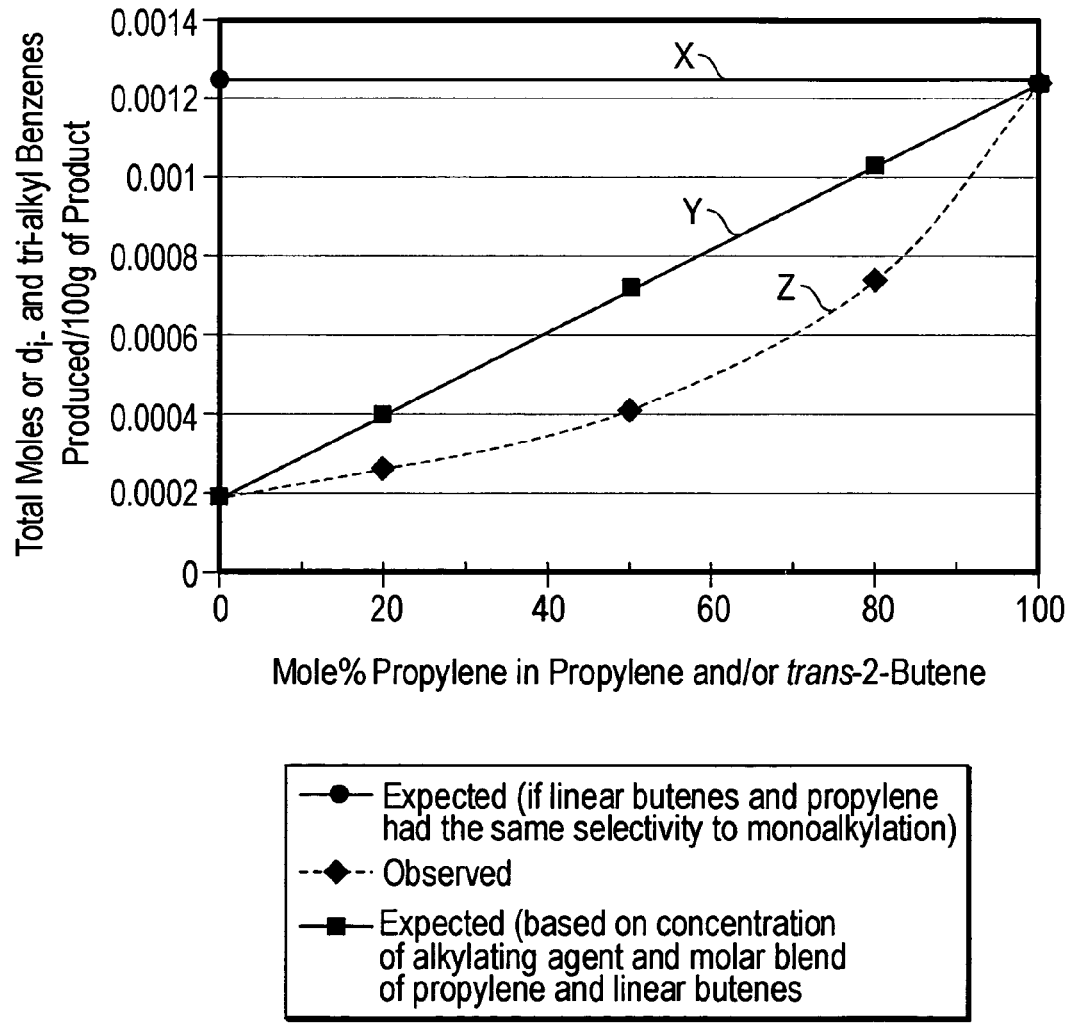
FIG. 1 is a chart illustrating the expected vs. observed amounts of di- and tri-alkyl benzenes formed during the alkylation of benzene with propylene and/or trans-2-butene.

FIG. 1 is a chart illustrating the predicted vs. observed amounts of di- and tri-alkyl benzenes formed during the alkylation of benzene with propylene and/or trans-2-butene at varying molar ratios using zeolite beta alkyation catalyst. A surprising increase in selectivity to monoalkylation was observed when the alkylating agent was a combination of propylene and one or more linear butene(s).

If linear butene(s) and propylenes had the same selectivity to alkylation as observed for propylene, the predicted total moles of di- and tri-alkyl benzenes produced per 100 g of product would be the same—regardless of whether the alkylation agent is propylene and/or linear butene(s). This prediction appears as line "X" on FIG. 1.

Surprisingly, the amount of di- and tri-alkyl benzenes actually observed using 100 mole % trans-2-butene as the alkylating agent was over 6 times less than the result observed using 100 mole % propylene as the alkylating agent. The actual amount of di- and tri-alkyl benzenes produced using 100 mole % propylene in Example 2 was 0.00124 moles per 100 g of product (far right data point on lines X and Y). The actual amount of di- and tri-alkyl benzenes produced using 100 mole % trans-2-butene in Example 4 was 0.00019 moles per 100 g of product (far left data point on line Y). The total moles of di- and tri-alkyl benzenes predicted when the molar ratio of propylene/trans-2-butene varied between these two points is illustrated by line "Y."

In addition to the surprising increase in selectivity, unexpected synergy was observed using a combination of linear butene(s) and propylene—particularly at concentrations of from about 20 mole % to about 80 mole % propylene. The curve "Z" on FIG. 1 is a plot of the actual selectivities found when the molar ratio of linear butylene and propylene were varied (Examples 5-7). Where the mole % propylene is from about 20 mole % to about 80 mole %, the actual moles of di- and tri-alkyl benzenes per 100 g product was at least about 30% less than the predicted amount (line Y). Similar results are expected using other linear butenes.

Using an alkylating agent comprising a combination of propylene and linear butene(s) increases the yield of monoalkylated cumene and s-butylbenzene. The process may eliminate or at least reduce the size of any required transalkylator, thereby decreasing equipment costs and simplifying the process.

Zeolite Beta

The method involves contacting the aromatic hydrocarbon and alkylating agent with zeolite beta. Zeolite beta is a synthetic crystalline aluminosilicate. See U.S. Pat. No. 3,308,069 and Re 28,341, incorporated herein by reference. Zeolite beta is identified by its characteristic X-ray diffraction pattern which, in terms of the significant d values (Ångstroms, radiation:K alpha doublet of copper, Geiger counter spectrometer), is reproduced in Table 1 below.

TABLE 1 d Values of Reflection in Zeolite Beta 11.4 ± 0.2
7.4 ± 0.2
6.7 ± 0.2
4.25 ± 0.1
3.97 ± 0.1
3.0 ± 0.1
2.2 ± 0.1

The composition of zeolite beta is described as follows:

wherein M is a metal cation; $R^1$ is selected from the group consisting of aluminum, gallium, boron, and iron (preferably aluminum); $R^2$ is selected from the group consisting of silicon, germanium, and phosphorous (preferably silicon); X is less than 1, preferably less than 0.75, TEA represents tetraethylammonium ion; Y is greater than 5 and less than 100, and W is up to about 4, depending on the condition of dehydration and on the metal cation present.

Suitable metal cations (M) are typically a sodium ion from the original synthesis but may also be a metal ion added by ion exchange techniques. Suitable metal ions include those from Groups IA, IIA or IIIA of the Periodic Table of the Elements. Another way to define suitable metal ions (M) is as a transition metal. Examples of suitable ions include ions of lithium, potassium, calcium, magnesium, barium, lanthanum, cerium, nickel, platinum, palladium, and combinations thereof. When the Periodic Table of the Elements is referred to herein, the source of the Periodic Table is: F. Cotton et al. Advanced Inorganic Chemistry (5th Ed. 1988).

See also European Patent Application Nos. 95,304, 159, 846, 159,847, and 164,939, incorporated herein by reference, which have broadened the definition of zeolite beta to include materials prepared using templating agents other than tetraethylammonium hydroxide and materials having $R^2/R^1$ (preferably Si/Al) atomic ratios greater than 100. Also, the zeolites described in European Patent Applications Nos. 55,046 ("Nu-2") and 64,328 and British Patent Application No. 2,024,790 ("Boralite B"), incorporated herein by reference, have structures and X-ray diffraction patterns very similar to that of zeolite beta and are included within the scope of the term "zeolite beta", as used herein.

The forms of zeolite beta which are most useful herein are crystalline aluminosilicates having the empirical formula:

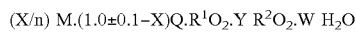

wherein $R^1$ is selected from the group consisting of aluminum, gallium, boron, and iron (preferably aluminum); $R^2$ is selected from the group consisting of silicon, germanium, and phosphorous (preferably silicon); X is less than 1, preferably less than 0.75, Y is greater than 5 and less than 100, W is up to about 4, M is a metal ion, n is the valence of M, and Q is selected from the group consisting of hydrogen ion, ammonium ion, organic cation, and mixtures thereof. In a preferred embodiment, Y is preferably greater than 5 and less than about 50. Consequently, the silicon to aluminum atomic ratio in the above formula is greater than 5:1 and less than 100:1, and preferably greater than 5:1 and less than about 50:1.

M preferably is selected from the group consisting of sodium, potassium, lithium, and cesium, even more preferably sodium and potassium, and most preferably sodium.

Suitable organic cations are those cations which are derived in aqueous solution from tetraethyl-ammonium bromide or hydroxide, dibenzyl-1,4-diazabicyclo [2.2.2]octane chloride, dimethyldibenzyl ammonium chloride, 1,4-di(1-azonium bicyclo[2.2.2]-octane) butane dibromide or dihydroxide, and the like. See European Patent Applications Nos. 159,846 and 159,847, and U.S. Pat. No. 4,508,837, incorporated herein by reference. A preferred organic cation is tetraethyl-ammonium ion.

The zeolite beta preferably is predominantly in its hydrogen ion form. Generally, the zeolite is converted to its hydrogen form by ammonium exchange followed by calcination. If the zeolite is synthesized with a high enough ratio of organonitrogen cation to sodium ion, calcination alone may be sufficient. It is preferred that, after calcination, a major portion of the cation sites are occupied by hydrogen ions and/or rare earth ions. It is especially preferred that at least 80% of the cation sites are occupied by hydrogen ions.

Highly active zeolite beta catalyst suitable for use in the present application include, but are not necessarily limited to zeolite beta made using the procedures described in U.S. Pat. No. 5,258,570, incorporated herein by reference. U.S. Pat. No. 5,258,570 describes a method in which zeolite beta is (a) calcined at a temperature in the range of from about 200° C. to 1000° C., in order to remove a substantial portion of catalyst templating agent, and (b) the calcined catalyst is ion exchanged with a salt solution comprising one or more hydrogen forming cation selected from the group consisting of —$NH_4$ and quaternary ammonium. For example, an aqueous ammonium nitrate solution can be used to ion exchange the beta zeolite.

The zeolite H-beta generally is available as a powder. The zeolite beta powder preferably: comprises about 0.1 wt. % or less alkali metal oxide, more preferably less than about 0.02 wt. % $Na_2O$; has a molar silica to alumina ratio of from about 15 to about 100, preferably from about 20 to about 25; and has a surface area of about 500 $m^2/g$ or more, preferably about 670 $m^2/g$ or more.

The pure zeolite may used as a catalyst, but generally it is preferred to mix the zeolite powder with an inorganic oxide binder such as alumina, silica, silica/alumina, or naturally occurring clays. A preferred inorganic binder is alumina. The catalyst/binder mixture preferably is formed into particles having substantially any form, including but not necessarily limited to spherical forms, tablet forms, cylindrical forms, multi-lobed cylindrical forms, cylindrical rings, and their corresponding hollow counterparts.

Where the catalyst particles comprise a binder, the catalyst particles comprise a sufficient quantity of zeolite beta to render the resulting particles catalytically active. Suitably, the catalyst particles comprise from about 1 wt. % to about 99 wt. % zeolite beta, more typically from about 10 wt. % to about 90 wt. % zeolite beta, even more typically from about 60 wt. % to 90 wt. % zeolite beta, based on the total weight of the catalyst particles.

Suitable commercially available zeolite beta catalyst includes, but is not limited to CP 786, available from Zeolyst International.

In a preferred embodiment, the zeolite beta catalyst comprises extrudates comprising about 80 wt. % beta zeolite in hydrogen form and about 20 wt. % alumina binder. In a preferred embodiment, zeolite beta powder used to form the extrudates preferably has the following generally properties:

| Zeolite H-Beta Powder Properties | |
|---|---|
| Na$_2$O, % wt | 0.02% |
| Molar Silica to Alumina ratio | 21.2 |
| Surface Area, m2/g | 670 m2/g |

In a preferred embodiment, the extrudates have the following general properties:

| Extrudate Properties | |
|---|---|
| Average Length, mm | 4.2 mm |
| Average Diameter, mm | 1.62 mm |
| Crush Strength (anvil), lb/mm | 3.0 lb/mm |
| Compacted Bulk Density, lb/ft3 | 27.5 lb/ft3 |
| Surface Area, m2/g | 550 m2/g |
| Loss on ignition (LOI)*, % wt | 2.8% |

*dried at 700° C.

In a most preferred embodiment, the extrudates comprise cylinders having an average length of from about 3.0 mm to about 8 mm, and an average diameter of from about 0.5 mm to about 8 mm. A preferred average diameter is about 1.6 mm.

The Aromatic Hydrocarbon

Although the method is particularly useful when the alkylation agent is used to alkylate benzene, substituted benzene also may be alkylated using the method. Suitable substituted benzene comprises one or more substituent which does not interfere with the production of primarily monoalkylated aromatic compound. An example of such substituents includes, but is not necessarily limited to hydroxyl groups. Mixtures of aromatic hydrocarbons also may be alkylated.

The benzene feedstream suitably comprises about 95 wt. % or more, preferably about 98 wt. % or more, more preferably about 99 wt % or more benzene, as determined by gas chromatographic analysis. The remainder suitably comprises toluene and other trace impurities, preferably from conventional benzene manufacturing processes, such as aromatics reforming and benzene extraction. The use of the term "consisting essentially of" is not intended to exclude trace impurities found in such streams. See Robert A. Meyers, *Handbook of Petroleum Refining Processes*, McGraw Hill (3rd Ed. 2004), incorporated herein by reference.

The Alkylating Agent

The alkylating agent comprises propylene and linear butene(s), which are available from a variety of sources. Suitable linear butenes are selected from the group consisting of butene-1, trans-2-butene, cis-2-butene, and mixtures thereof. A preferred linear butene is trans-2-butene, which is available from a variety of sources, including but not necessarily limited to Scott Specialty Gases. In a preferred embodiment, the alkylating agent preferably is from about a 1:4 to about a 4:1 molar blend of propylene to linear butene(s).

It is preferable to use linear butene(s) having about 2000 ppm or less isobutylene, preferably about 500 ppm or less isobutylene, more preferably about 100 ppm or less isobutylene. Lower contents of isobutylene in the linear butene(s) results in lower amounts of t-butylated product, which may be difficult to separate from the desired s-butylated product.

The alkylating agent typically comprises some alkanes, diolefins, and alkynes. Preferably, the quantity of diolefins and/or alkynes is about 500 ppm or less, more preferably about 200 ppm or less, most preferably about 100 ppm or less. Cycloparaffins, such as cyclopropane and cyclobutane, also may be present in the feed. Preferably, the amount of cyclopropane and/or cyclobutane in the feed is about 1000 ppm or less, more preferably about 300 ppm or less, most preferably about 100 ppm or less.

The Alkylation Process

Various types of reactors may be used in the process. For example, the process may be carried out in batchwise fashion by adding the catalyst and aromatic feedstock to a stirred autoclave, heating to reaction temperature, and then slowly adding the olefinic or polyalkylaromatic feedstock. A heat transfer fluid may be circulated through the jacket of the autoclave, or a condenser may be provided, to remove the heat of reaction and maintain a constant temperature. The process also may be performed in a catalytic distillation mode. See e.g. U.S. Pat. Nos. 5,345,006; 5,262,576; 5,221,441; 5,204,064; 5,176,883; 5,120,403; 4,978,807; 4,950,834; each of which is incorporated herein by reference.

Large scale industrial processes may employ a fixed bed reactor operating in an upflow or downflow mode or a moving bed reactor operating with concurrent or counter-current catalyst and hydrocarbon flows. These reactors may contain a single catalyst bed or multiple catalyst beds and may be equipped for the interstage addition of olefins and interstage cooling. Interstage olefin addition and more nearly isothermal operation enhance product quality and catalyst life. A moving bed reactor makes possible the continuous removal of spent catalyst for regeneration and replacement by fresh or regenerated catalysts.

In a preferred embodiment, the alkylation process is carried out with addition of aromatic feedstock in at least two stages. Preferably, there will be two or more catalyst beds or reactors in series, wherein at least a portion of the aromatic feedstock is added between the catalyst beds or reactors. Interstage cooling may be accomplished by the use of a cooling coil or heat exchanger.

For convenience, the reactors may sometimes be referred to as "columns" and the product stream produced by the reactor may be referred to as a "column stream." Reference to the reactor or the reactor product as a column or column product should not be construed as limiting the claims to the use of a particular type of reactor.

The alkylation preferably is conducted using a fixed bed reactor operating under at least partial liquid phase conditions. The total liquid feedrate to the alkylator is from about 40 g/hr to about 200 g/hr for about 25 g total weight of zeolite beta catalyst, including binder. In order to maintain at least a partial liquid phase and to minimize skeletal isomerization of linear butene(s) to isobutylene, the temperature in the reaction vessel is maintained at from about 100° C. to about 150° C., preferably at from about 110° C. to about 145° C., most preferably at from about 120° C. to about 140° C. The pressure in the reaction vessel will vary with the temperature, but generally is from about 250 psig to about 350 psig, preferably from about 270 psig to about 325 psig.

The desired level of conversion may vary. The process preferably is continued to achieve 50% or more, preferably 95% or more, more preferably 99% or more, most preferably 99.9% or more conversion of both propylene and linear butene(s).

Although propylene and linear butene(s) can be converted in essentially quantitative yield, the selectivity to the respective monoalkylated products differs. Use of a combination of propylene and linear butene(s) as the alkylating agent produces less than the projected total moles of di- and tri-alkyl benzenes per 100 g product predicted under a given set of conditions. At molar ratios of propylene:linear butene(s) of from about 1:4 to about 4:1, the process produces at least about 10% less, preferably at least about 20% less, more preferably at least about 30% less than the projected total moles of di- and tri-alkyl benzenes per 100 g product predicted under the given conditions, as shown in FIG. 1.

Stated another way, the process produces selectivity to sec-butylbenzene of 98% or more, preferably 99% or more, more preferably 99.5% or more, and selectivity to cumene of about 95% or more, preferably 97% or more.

Process Configurations

A number of configurations for running the process with and without a transalkylator are depicted in FIGS. 2-9, which are flow diagrams of variations on the process in which various reactors are depicted as boxes.

FIGS. 2-5 depict various process configurations in which a transalkylator is used in parallel with an alkylator.

Figure 2:
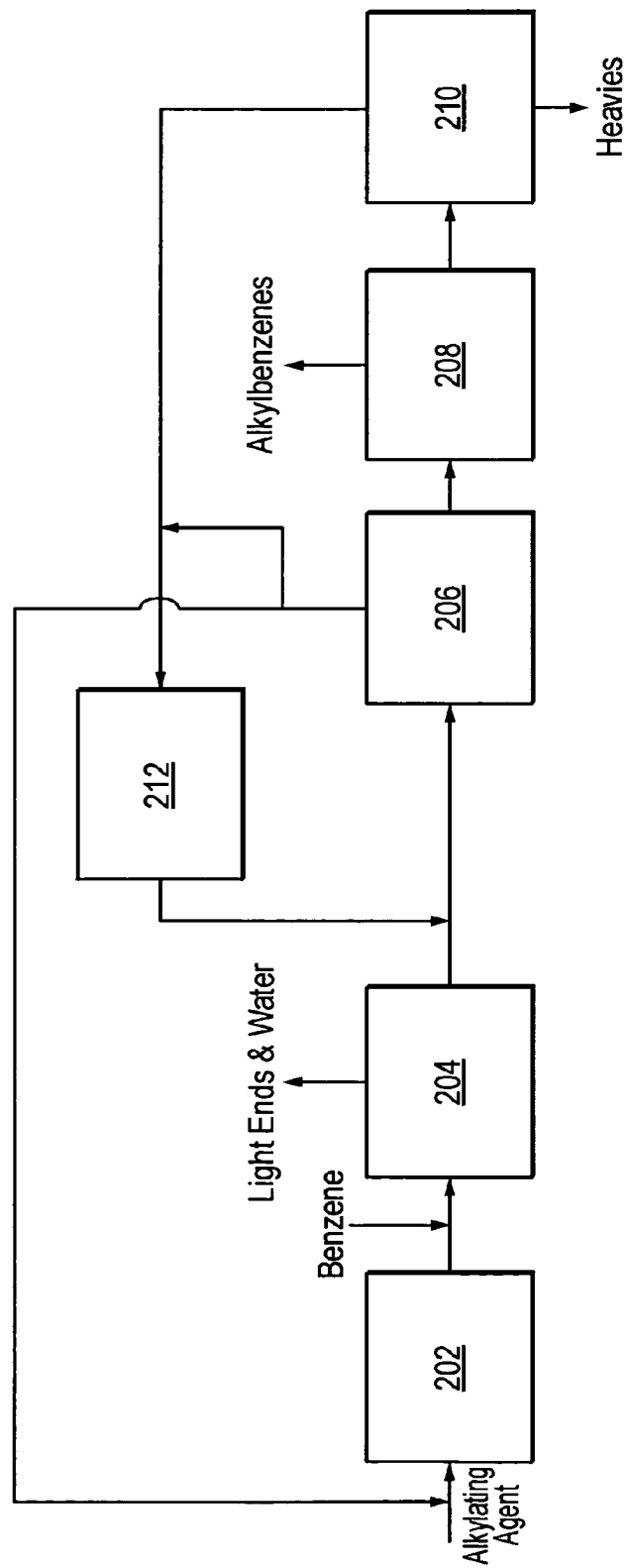
FIG. 2 is a flow diagram of a "base case" process configuration comprising a transalkylator in parallel with the alkylator.

Referring to FIG. 2, recycled benzene and alkylating agent are fed to an alkylator 202. Fresh benzene, which may include some moisture, is fed along with the alkylator stream to a light ends column 204. Light ends and water are purged, leaving a light ends column stream, which is fed to a benzene column 206. Also fed to the benzene column is the transalkylation stream, discussed below. Benzene is recovered from the benzene column 206, leaving a benzene-depleted benzene column stream, which is fed to the alkyl benzene column 208. Monoalkylated benzene is collected from the alkyl benzene column 208 as a final product, leaving an alkyl benzene column stream, which is fed to a dialkyl benzene column 210. Heavies are removed from the dialkyl benzene column 210, and the dialkyl benzene column stream is fed to the transalkylator 212, along with the recovered benzene from the benzene column 206. In the transalkylator 212, an alkyl group from a molecule of multialkyl benzene, preferably dialkyl benzene, is used to transalkylate a virgin benzene molecule and to produce a transalkylation product stream comprising excess benzene and monoalkylated benzene molecules. The transalkylation stream is fed to the benzene column 206.

Figure 3:
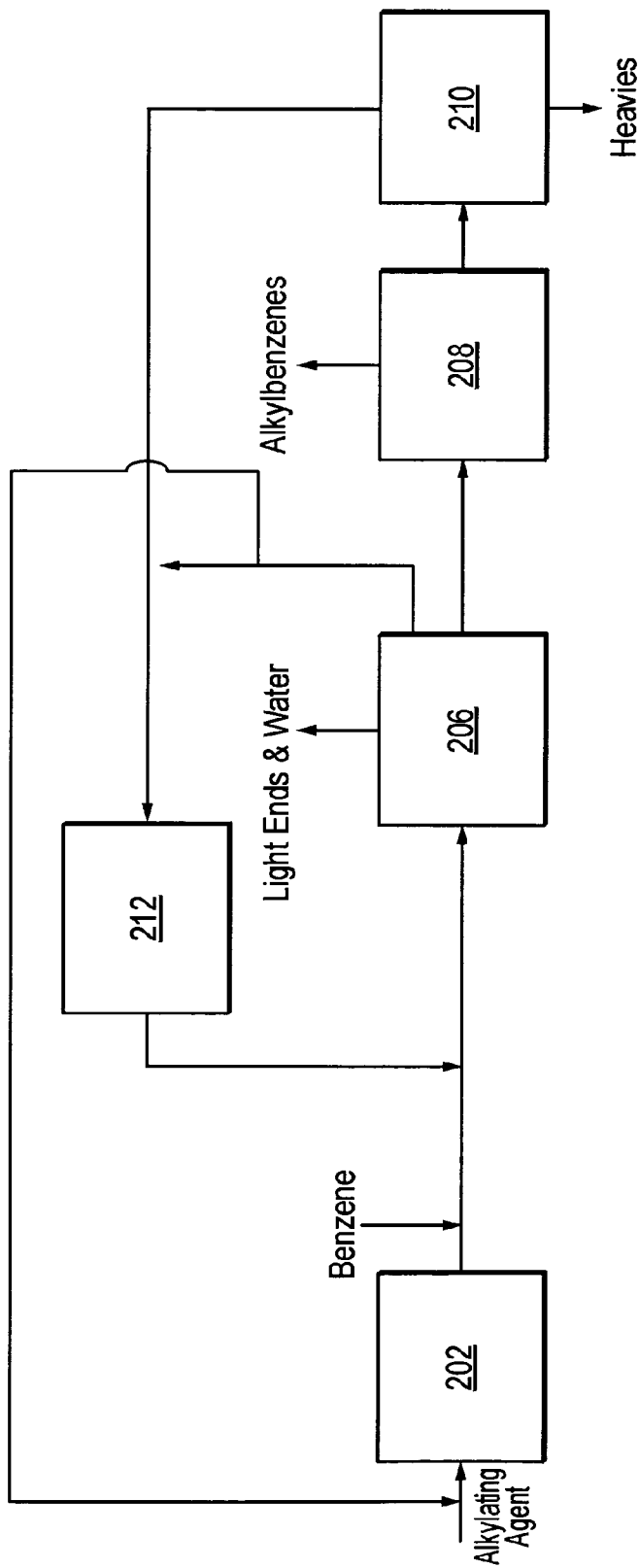
FIG. 3 is a flow diagram of the "base case" process configuration of FIG. 2 with no separate light ends column and with an optional benzene column pasteurization section (which also may be applied to other process configurations).

FIG. 3 is a flow diagram of a process which reduces equipment cost by eliminating the light ends column (204 in FIG. 2). In this embodiment, light ends and water are fed from the alkylator 202 along with the alkylation product directly to the benzene column 206. The light ends and water are purged from the benzene column 206, and benzene is recovered from the benzene column and fed to the transalkylator 212. The benzene column stream is fed to the alkyl benzene column 208. The remainder of the process is the same as described with respect to FIG. 2.

Figure 4:
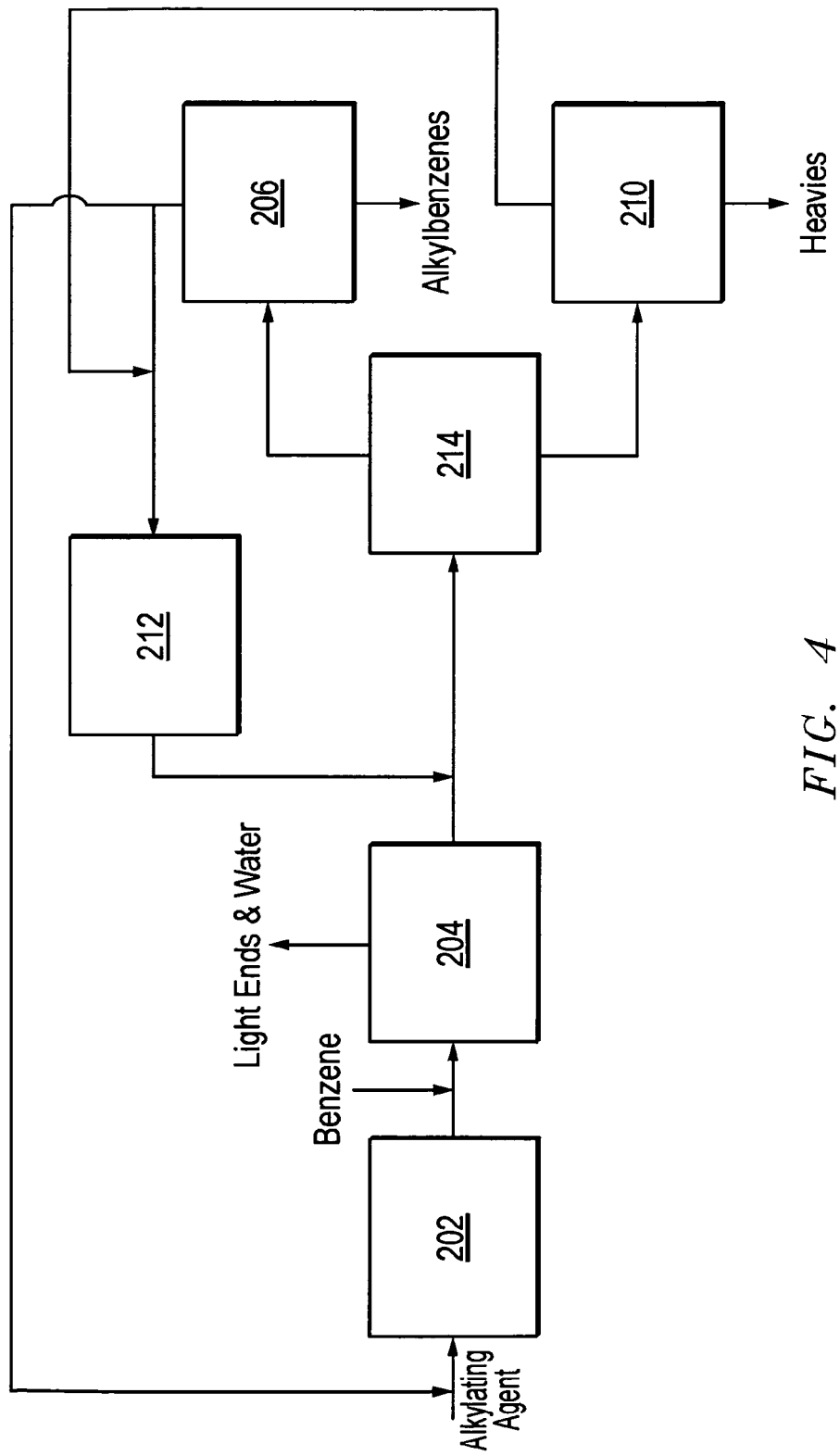
FIG. 4 is a flow diagram of a process configuration using an alkylate splitter column.

FIG. 4 is a flow diagram of the process using an alkylate splitter column 214. In this embodiment, benzene recovered from the benzene column 206 is fed to the alkylator 202, along with alkylating agent. Fresh benzene is fed along with the alkylator stream to a light ends column 204. Light ends and water are purged in the light ends column and the light ends column stream is fed to an alkylate splitter column 214. The transalkylation stream also is fed to the alkylate splitter column 214. The feedstream to the alkylate splitter column 214 is separated into a lighter material, which is fed to the benzene column 206 and a heavier material which is fed to the dialkylbenzene column 210. Heavies are removed from the dialkyl benzene column 210, and the dialkyl benzene column stream is fed to the transalkylator 212. Recovered benzene is fed from the benzene column 206 to the transalkylator 212, and the final alkylbenzene product is collected from the benzene column 206.

Figure 5:
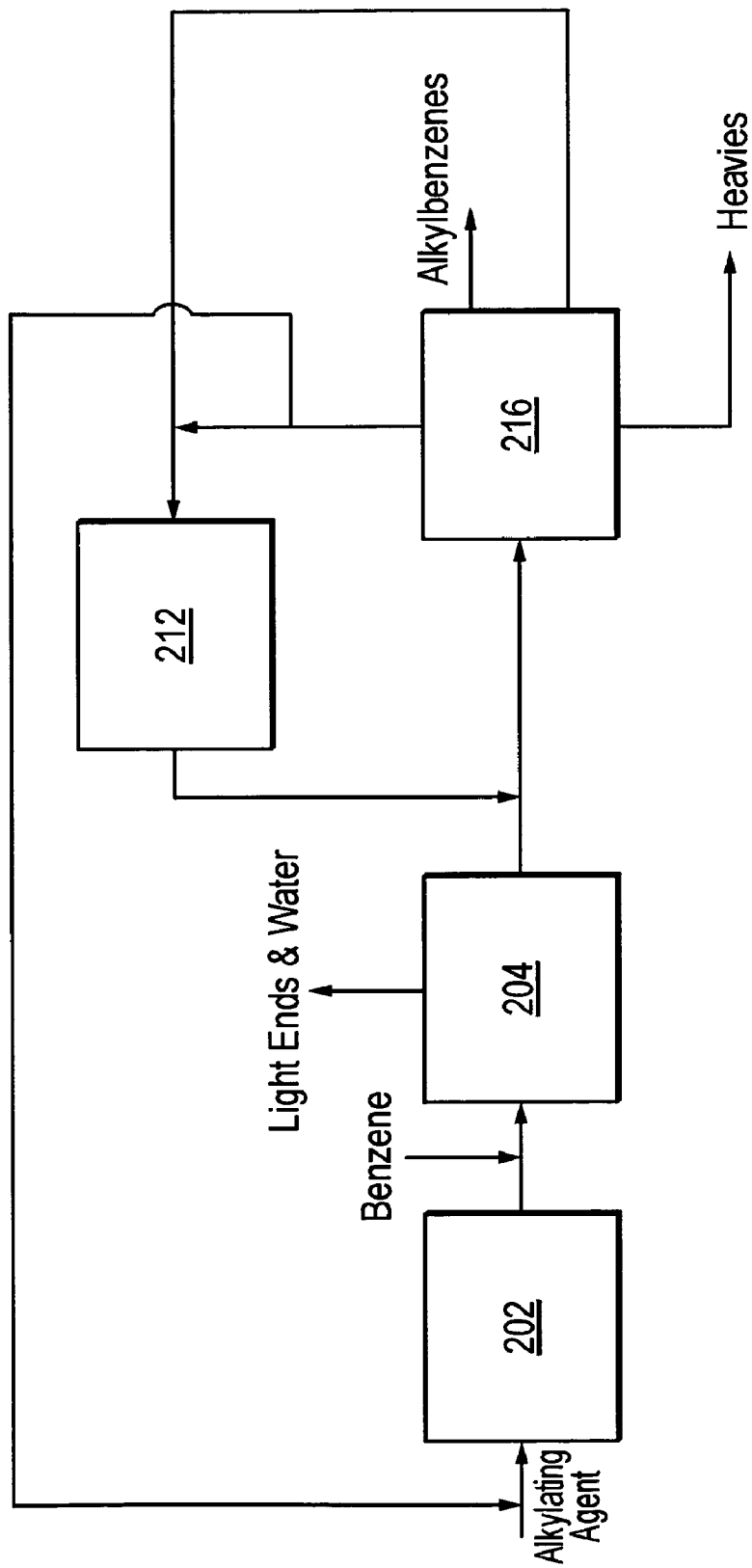
FIG. 5 is a flow diagram of a process configuration using a divided wall column.

FIG. 5 is a flow diagram of the process using a divided wall column 216 in place of: (a) the benzene column 206; (b) the alkyl benzene column 208; and, (c) the dialkyl benzene column 210. In this embodiment, recycled benzene and alkylating agent are fed to an alkylator 202. Fresh benzene, which may include some moisture, is fed along with the alkylated product to a light ends column 204. Light ends and water are purged in the light ends column and the remainder is fed to the divided wall column 216. Heavies are removed from the divided wall column 216. The final alkylbenzene product is recovered as a separate stream from the divided wall column 216. Benzene is recovered as a separate stream from the divided wall column and fed to the transalkylator 212. Multialkylated benzenes also are recovered as a separate stream from the divided wall column 216 and fed to the transalkylator 212.

Figure 6:
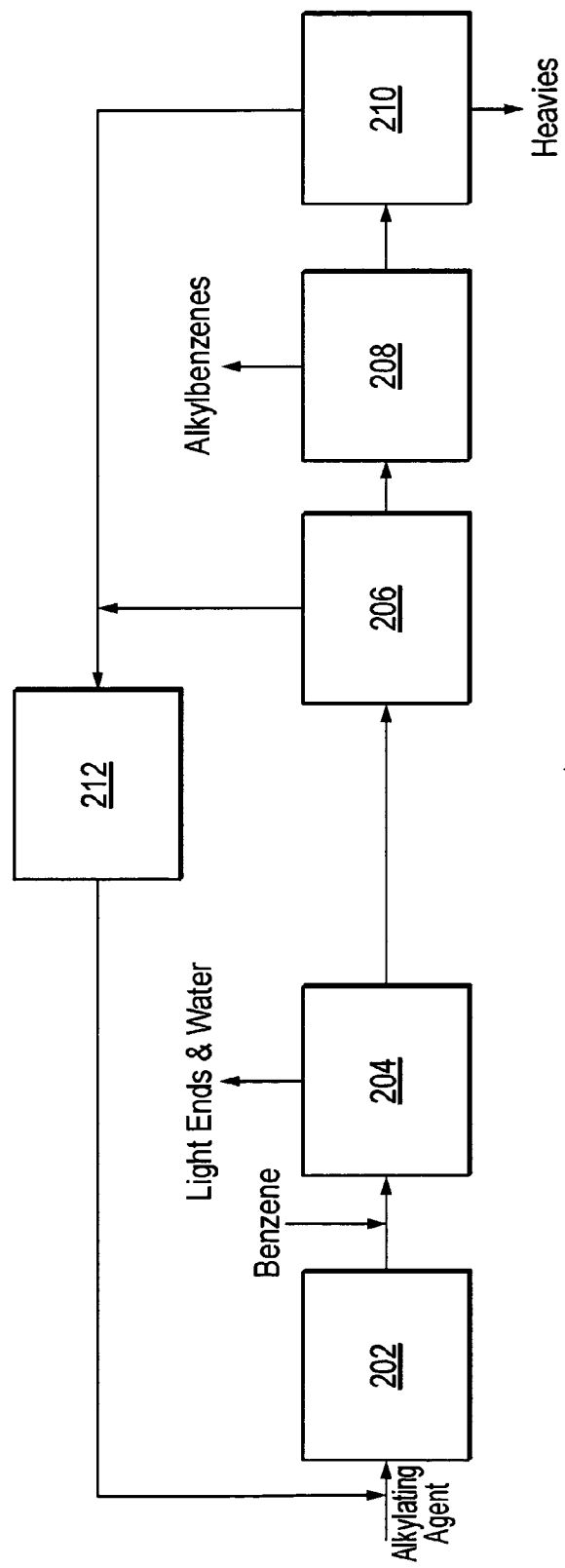
FIG. 6 is a flow diagram of a process configuration in which the transalkylator precedes the alkylator.
Figure 7:
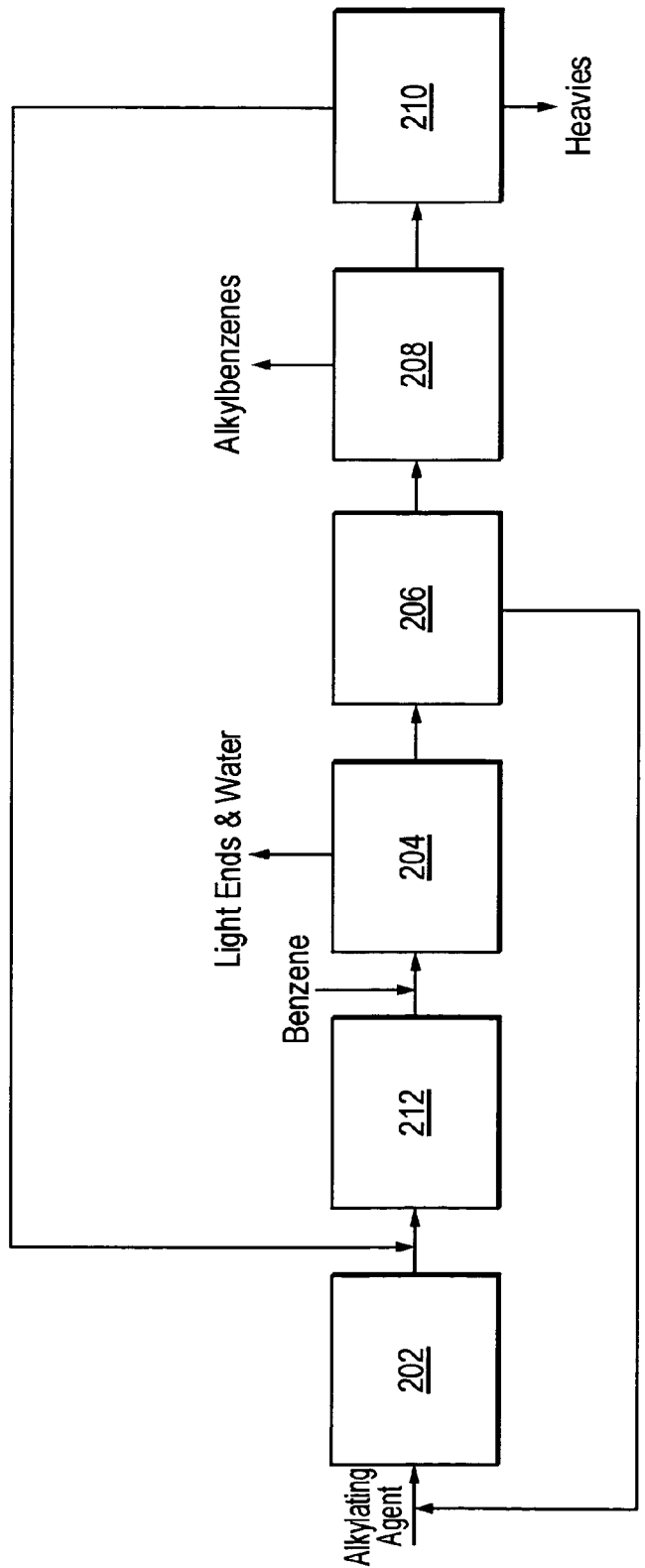
FIG. 7 is a flow diagram of a process configuration in which the transalkylator is located immediately downstream of the alkylator.
Figure 8:
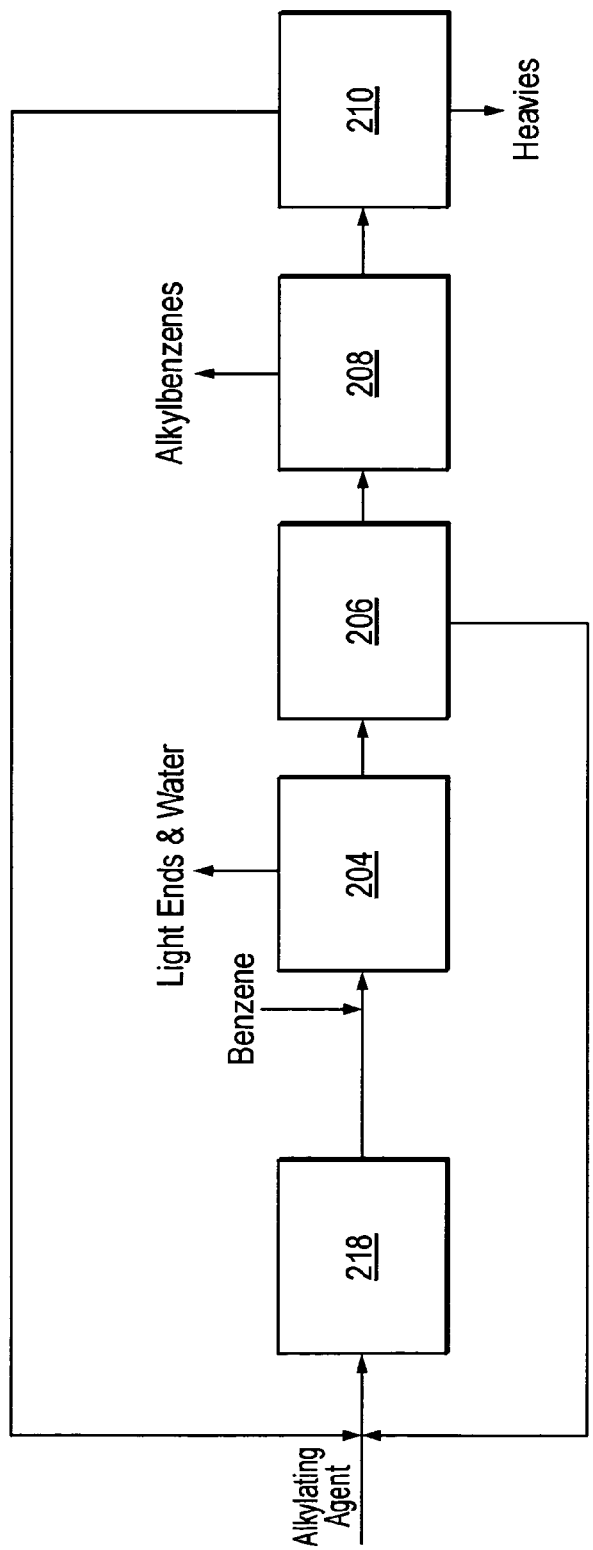
FIG. 8 is a flow diagram of a process configuration using an alkylator/transalkylator.

FIGS. 6-8 depict procedures in which there either is no transalkylator 212, there is a combined alkylator/transalkylator 218 (FIG. 8), or the transalkylator 212 runs in series with the alkylator 202.

FIG. 6 is a flow diagram of the process in which the transalkylator 212 is in series with the alkylator 202. In this embodiment, alkylating agent and the transalkylator stream are fed to the alkylator 202. The alkylator stream and fresh benzene are fed to the light ends column 204. Light ends and water are purged in the light ends column 204 and the light ends column stream is fed to a benzene column 206. Benzene is recovered from the benzene column and fed to the transalkylator 212. The final monoalkylated benzene product(s) are withdrawn from the alkyl benzene column 208, and the remaining benzene column stream is fed to the dialkyl benzene column 210. Heavies are removed from the dialkyl benzene column 210, and the dialkyl benzene column stream is fed to the transalkylator 212, along with the recovered benzene from the benzene column 206. The transalkylation stream is fed to the alkylator 202.

FIG. 7 is a flow diagram of a procedure in which benzene recovered from the benzene column 206 is fed to the alkylator 202 along with alkylating agent. The alkylator column stream is fed to the transalkylator 212, along with dialkyl benzene recovered from the dialkyl benzene column 210. Fresh benzene is fed along with the transalkylator stream to a light ends column 204. Light ends and water are purged in the light ends column and the light ends column stream is fed to the benzene column 206. After recovery of benzene, the benzene column stream is fed to the alkylbenzene column 208. Heavies are removed from the alkyl benzene column 208, and the final alkylbenzene product is collected from the alkylbenzene column 208. The alkylbenzene column stream is fed to the dialkyl benzene column 210. Heavies are removed, and the resulting dialkyl benzene column stream is fed to the transalkylator 212.

FIG. 8 is a flow diagram of a procedure using an alkylator/transalkylator 218. Benzene recovered from the benzene column 206 is fed to the alkylator/transalkylator 218 along with alkylating agent and dialkyl benzene from the dialkyl benzene column 210. Generally, the alkylator/transalkylator 218 comprises two catalyst beds, one bed comprising zeolite beta for monoalkylation of benzene, and one bed comprising transalkylation catalyst. Benzene is alkylated by the zeolite beta, and dialkyl benzene(s) are transalkylated by the second catalyst bed. Suitable catalyst for transalkylation include, but are not necessarily limited to large pore zeolites (preferably having an average pore diameter of about 7 Å or more, more preferably more than 7 Å), such as zeolite Y, boron trifluoride, liquid and solid phosphoric acid, and sulfuric acid. Beta zeolites are useful for transalkylating di- and tri-isopropyl benzene, but do not work as well in transalkylating di-sec-butylbenzenes. Preferred transalkylation catalysts are Y zeolite and solid phosphoric acid.

Further referring to FIG. 8, the alkylator/transalkylator stream is fed, along with fresh benzene, to a light ends column 204. Light ends and water are purged in the light ends column 204 and the light ends column stream is fed to the benzene column 206. Benzene is recovered from the benzene column 206 and fed to the alkylator/transalkylator 218. The remaining benzene column stream is fed to the alkylbenzene column 208. The final alkylbenzene product is removed from the alkylbenzene column 208, and the remaining alkylbenzene stream is fed to the dialkyl benzene column 210. Heavies are removed from the dialkyl benzene column 210, and the dialkyl benzene column stream is fed to the alkylator/transalkylator 218.

Figure 9:
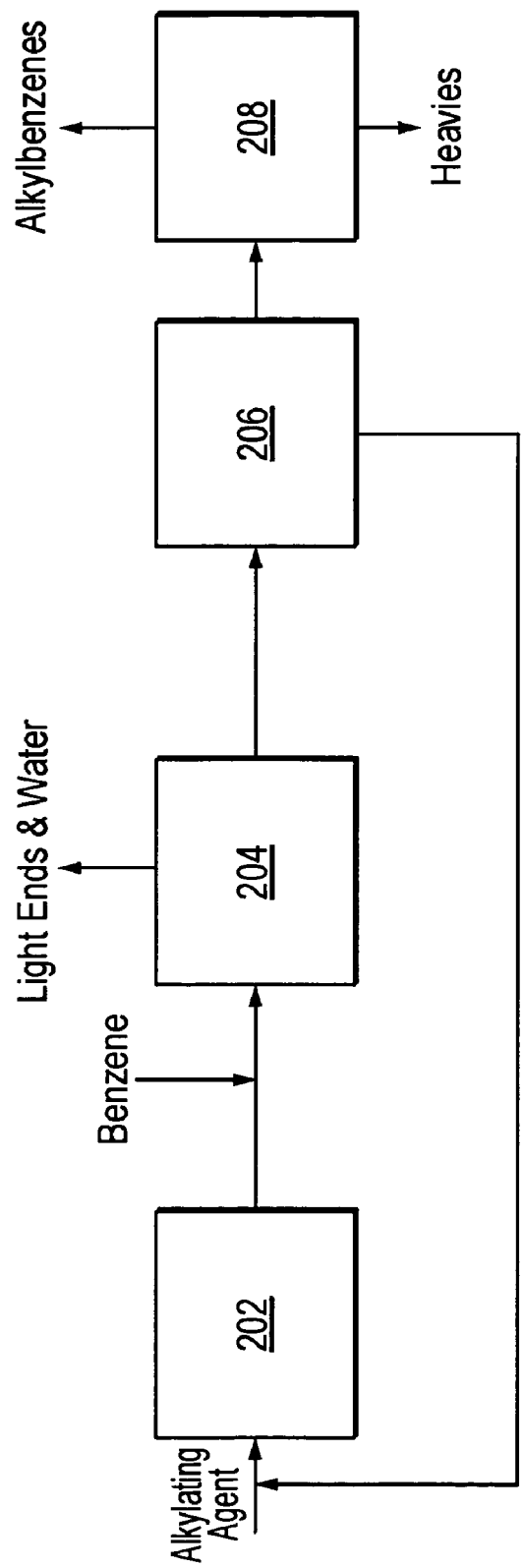
FIG. 9 is a flow diagram of a process configuration which does not include a transalkylator or a dialkylbenzene column.

FIG. 9 is a flow diagram of a procedure which does not use a transalkylator 212. In this process, alkylating agent and benzene recovered from the benzene column are fed to the alkylator 202. Generally, the alkylator 202 comprises two catalyst beds, one bed comprising zeolite beta for monoalkylation of benzene, and one bed comprising transalkylation catalyst.

The alkylator/transalkylator stream is fed, along with fresh benzene, to a light ends column 204. Light ends and water are purged in the light ends column 204 and the light ends column stream is fed to the benzene column 206. Benzene is recovered from the benzene column 206 and the benzene column stream is fed to the alkylbenzene column 208. Heavies are removed and the final alkylbenzene product is removed from the alkylbenzene column 208.

Modifications may be made to the foregoing embodiments, including but not necessarily limited to the following. Benzene can be introduced directly to the alkylator and/or transalkylator if the benzene is not too "wet." Other columns/reactors may be used depending on the quality of the feeds. For example, a column may be placed between the benzene column 206 and the alkylbenzene column 208 to remove ethylbenzene if there is too much ethylene in the olefin feed, or if too much ethylene is made in the alkylator or the transalkylator. The recycle benzene may be provided with a purge stream to prevent the build-up of nonaromatics, which may be formed in the reactors (e.g., propylene dimer) or present in the fresh benzene (e.g., methyl pentanes). And, the benzene and/or olefin feeds may be treated to remove deleterious impurities.

The process has been run for over 2,500 hours without noticeable deactivation of the zeolite beta catalyst. As conversion efficiency decreases, the catalyst either may be replaced or regenerated. Regeneration generally is accomplished by hot hydrogen stripping or by oxidative regeneration at elevated temperature using oxygen containing gas streams, such as air or oxygen diluted in nitrogen blends.

Preferably, the reagents are stored under conditions which avoid contamination. In a preferred embodiment, the reagents are stored under dry nitrogen and transferred directly to the reactor to avoid any contamination.

The application will be more clearly understood with reference to the following examples, which are illustrative only and should not be construed as limiting the claims.

Conditions

Alkylation tests were performed using mixtures of propylene and various olefins having four carbon atoms using the following procedures and materials.

Catalyst

The zeolite beta powder used in the following examples was CP 814E, a zeolite beta powder comprising zeolite in the hydrogen form, commercially available from Zeolyst International. The actual zeolite beta powder used in the following Examples had the following properties:

| | |
|---|---|
| $Na_2O$, % wt | 0.02% |
| Molar Silica to Alumina ratio | 21.2 |
| Surface Area, $m^2/g$ | 670 $m^2/g$ |

A mixture of 80 wt. % zeolite beta powder and 20 wt. % alumina binder was formed and extruded to form extrudates having the following properties:

| | |
|---|---|
| Average Length, mm | 4.2 mm |
| Average Diameter, mm | 1.62 mm |
| Crush Strength (anvil), lb/mm | 3.0 lb/mm |
| Compacted Bulk Density, $lb/ft^3$ | 27.5 $lb/ft^3$ |
| Surface Area, $m^2/g$ | 550 $m^2/g$ |
| LOI, % wt | 2.8% |

The catalyst used in the following examples was in the form of cylinders having an average diameter of 1.6 mm. The product is available from Zeolyst International under the name CP786.

Reagents

Benzene was obtained from Aldrich Chemical Company while propylene and butenes (trans-2-butene or isobutylene) were obtained from Scott Specialty Gases. The reagents were stored under dry nitrogen and transferred directly to the reactor to avoid contamination.

Laboratory Alkylation Microreactor

A microreactor for studying the alkylation of benzene with olefins having three and/or four carbon atoms was constructed to operate in a downflow, liquid filled mode. In each experiment, benzene and the light olefin(s) were pumped into the reactor with the aid of a Beckman high pressure liquid chromatography (HPLC) pump. The olefin and benzene mixture was then allowed to react over the acidic zeolite beta catalyst at the desired reaction conditions.

The reactor tube was made of 316 SS and equipped with 416 SS heads to minimize galling. The reactor tube was 68.58 cm (27 inches) long and had a 2.54 cm (1.00 inch) outer diameter and a 1.47 cm (0.58 inch) inner diameter. A thermowell running up the center of the reactor tube was connected at the bottom of the reactor. The thermowell housed a 7-point thermocouple during operation which monitored the temperatures at 7 evenly spaced positions inside the reactor tube. A 60.96 cm (24 inch) long, 4-zone Lindberg furnace was used to heat the reactor tube.

After exiting the reactor tube, the gas and liquid products were analyzed using gas chromatography (GC), gas chromatography-mass spectroscopy (GC-MS) and nuclear magnetic resonance (NMR).

The reactor was loaded from the bottom. A small amount of glass wool was placed over the thermowell and pushed down the length of the tube. A bed of silicon carbide (20 mesh), was added so that when the catalyst bed was loaded, it resided near zone three and the top of zone four in the four zone furnace. After the 20 mesh SiC was loaded, another small plug of glass wool was added to hold the SiC in place. A total of 25.0 grams of zeolite beta catalyst was divided into four equal parts and mixed evenly with an equal weight of 60-80 mesh SiC. The four equal portions of catalyst and diluent were poured into the reactor tube while it was gently tapped. After the catalyst/SiC mixture was loaded, another piece of glass wool was inserted into the reactor. Enough 20 mesh SiC was then added to nearly fill the reactor. The remaining void was filled with a final plug of glass wool and a small, slotted, hollow metal spacer. During the reactor loading process, the thermowell stayed centered in the reactor tube. Once the reactor tube was properly filled, the top reactor head was installed and the multi-point gut thermocouple was inserted into the thermowell of the reactor.

Microreactor Operation

The reactor tube was placed in the furnace and all four of the furnace skin thermocouples were checked for proper positioning (in the middle of their corresponding heating zones) before closing the furnace. The hinged furnace door was closed and the two locking screws were tightened to ensure good contact between the reactor tube and the furnace. The reactor was then attached to the inlet and outlet piping of the reactor.

A T-fitting in the top head of the reactor allowed nitrogen gas to be added to the reactor during catalyst dryout to dry the catalyst. During operation, this gas line was blocked and only liquid feed was added to the reactor tube. The reactor was pressurized slowly to 5 psig and then a nitrogen flowrate of 10 liters/hour was established. The catalyst bed was heated to a bed temperature of 140° C. at a heating rate of 20° C. per hour and allowed to equilibrate for 16 hours at 140° C. The catalyst bed temperature was adjusted to the desired reaction temperature specified in the Example and then the reactor was pressurized slowly to the testing pressure by adjusting the pressure on the dome regulator. The nitrogen flow was stopped. The feed was introduced at the desired feed rate and the feed composition and the reactor products were sampled regularly to determine the conversion and selectivity by a variety of analytical methods (GC, GC/MS, NMR etc). The amounts of mono-alkylaromatics, di-alkylaromatics, and other products such as olefin oligomers were measured and quantified. A summary of the alkylation conditions used during the testing is presented in Table 1.

TABLE 1

Standard Aromatic Alkylation Testing Conditions

| | |
|---|---|
| Temperature: | 100-150° C. |
| Pressure: | 250-350 psig |
| Reactor Design: | Liquid phase, Down flow |
| Total Liquid Feedrate: | 40-200 g/Hr |
| Feedstock: | 1-4% wt. |
| Olefin(s) in Benzene Catalyst: | 25 g of 1.6 mm Cyl. CP 786 |

EXAMPLE 1

Reaction of Propylene with Benzene

Benzene and propylene were reacted over the CP 786 catalyst at the conditions outlined in Table 2. Complete conversion of the propylene was observed. The results of the testing are presented in Table 2. The product obtained was found to contain a significant amount of di-isopropyl benzenes isomers, such as 1,2 di-isopropyl benzene, (1,2-DIPB) 1,3 di-isopropyl benzene, (1,3-DIPB) and 1,4 di-isopropyl benzene (1,4-DIPB) and even some 1,3,5-tri-isopropyl benzene, (1,3,5-TIPB).

TABLE 2

Alkylation of Benzene with Propylene

| Conditions | | |
|---|---|---|
| Time on Stream, (hrs.) | | 119 |
| Temperature, (deg. C.) | | 133 |
| Operating Pressure, (psig) | | 291 |
| Total Olefin + Benzene Feedrate, (g/Hr) | | 151 |

| | Feedstock | Product |
|---|---|---|
| Propylene, (wt. %) | 1.211 | <0.001* |
| Propylene, (moles/100 g) | 0.0287 | * |
| Benzene, (wt. %) | 98.501 | 96.263 |
| Cumene, (wt. %) | <0.001* | 3.356 |
| 1,3-DIPB (wt. %) | <0.001* | 0.022 |
| 1,4-DIPB (wt. %) | <0.001* | 0.024 |
| 1,3,5-TIPB (wt. %) | <0.001* | 0.007 |
| % Conversion of Propylene | | >99.9 |
| % Selectivity to Cumene | | 97.0 |
| Total moles of di- and tri-propyl Benzenes produced/ 100 g of product | | 0.00038 |

*Not Detected by GC

EXAMPLE 2

Reaction of Propylene with Benzene

A higher concentration of propylene, (2.013 wt. %) than used in Example 1 was reacted with benzene over the CP 786 catalyst at similar conditions outlined in Table 3. Complete conversion of the propylene was observed. The results of the testing are presented in Table 3. The product obtained was found to contain higher amounts of the di-isopropyl benzenes isomers and 1,3,5-tri-isopropyl benzene.

TABLE 3

Alkylation of Benzene with Propylene

| Conditions | | |
|---|---|---|
| Time on Stream, (hrs.) | | 160 |
| Temperature, (deg. C.) | | 132 |
| Operating Pressure, (psig) | | 290 |
| Total Olefin + Benzene Feedrate, (g/Hr) | | 151 |

| | Feedstock | Product |
|---|---|---|
| Propylene, (wt. %) | 2.013 | <0.001* |
| Propylene, (moles/100 g) | 0.0478 | * |
| Benzene, (wt. | 97.731 | 94.002 |
| Cumene, (wt. %) | <0.001 | 5.485 |
| 1,3-DIPB (wt. %) | <0.001* | 0.074 |
| 1,4-DIPB (wt. %) | <0.001* | 0.083 |
| 1,3,5-TIPB (wt. %) | <0.001* | 0.023 |
| % Conversion of Propylene | | >99.9 |

TABLE 3-continued

Alkylation of Benzene with Propylene

| | |
|---|---|
| % Selectivity to Cumene | 95.4 |
| Total moles of di- and tri-propyl Benzenes produced/ 100 g of product | 0.00124 |

*Not Detected by GC

The total moles of di- and tri-propyl benzene in the product (0.00124) is the data point at the right end of line Y, and the data point at the right end of line X.

EXAMPLE 3

Reaction of trans-2-Butene with Benzene

Benzene and trans-2-butene were reacted over the CP 786 catalyst at the conditions outlined in Table 4. Complete conversion of the trans-2-butene was observed. The results of the testing are presented in Table 4. Sec-butyl benzene was formed in very high selectivity. Only small amounts of di-sec-butyl benzenes (DSBB) were observed. No tri-alkyl benzene was observed in the product.

TABLE 4

Alkylation of Benzene with trans-2-Butene

| Conditions | | |
|---|---|---|
| Time on Stream, (hrs.) | | 166 |
| Temperature, (deg. C.) | | 132 |
| Operating Pressure, (psig) | | 290 |
| Total Olefin + Benzene Feedrate, (g/Hr) | | 155 |
| | Feedstock | Product |
| trans-2-Butene, (wt. %) | 1.610 | <0.001* |
| trans-2-Butene, (moles/100 g) | 0.0287 | * |
| Benzene, (wt. %) | 98.049 | 95.846 |
| sec-Butyl Benzene, (wt. %) | <0.001* | 3.832 |
| 1,3-DSBB (wt. %) | <0.001* | 0.005 |
| 1,4-DSBB (wt. %) | <0.001* | 0.06 |
| 1,3,5-TSBB (wt. %) | <0.001* | <0.001* |
| % Conversion of trans-2-Butene | | >99.9 |
| % Selectivity to sec-Butyl Benzene | | 99.5 |
| Total moles of di- and tri-alkyl Benzenes produced/ 100 g of product | | 0.00006 |

*Not Detected by GC

EXAMPLE 4

Reaction of trans-2-Butene with Benzene

After over 2425 hours of operation, benzene and a higher concentration of trans-2-butene were reacted over the CP 786 catalyst at the conditions outlined in Table 5. Complete conversion of the trans-2-butene was observed. The results of the testing are presented in Table 5. Sec-butyl benzene was once again formed in very high selectivity with only small amounts of di-sec-butyl benzenes (DSBB) observed. No tri-alkyl benzene was observed in the product.

TABLE 5

Alkylation of Benzene with trans-2-Butene

| Conditions | | |
|---|---|---|
| Time on Stream, (hrs.) | | 2440 |
| Temperature, (deg. C.) | | 133 |

TABLE 5-continued

Alkylation of Benzene with trans-2-Butene

| | | |
|---|---|---|
| Operating Pressure, (psi) | | 288 |
| Total Olefin + Benzene Feedrate, (g/Hr) | | 156 |
| | Feedstock | Product |
| trans-2-Butene, (wt. %) | 2.681 | <0.001* |
| trans-2-Butene, (moles/100 g) | 0.0478 | * |
| Benzene, (wt. %) | 97.041 | 95.812 |
| sec-Butyl Benzene, (wt. %) | <0.001* | 3.832 |
| 1,3-DSBB (wt. %) | <0.001* | 0.010 |
| 1,4-DSBB (wt. %) | <0.001* | 0.026 |
| 1,3,5-TSBB (wt. %) | <0.001* | <0.001* |
| % Conversion of trans-2-Butene | | >99.9 |
| % Selectivity to sec-Butyl Benzene | | 99.0 |
| Total moles of di- and tri-alkyl Benzenes produced/ 100 g of product | | 0.00019 |

*Not Detected by GC

EXAMPLE 5

Reaction of a 1:1 Molar Blend of Propylene and trans-2-Butene with Benzene

An olefin blend of 50% propylene and 50% trans-2-butene (on a molar basis) was reacted over the CP 786 catalyst at the conditions outlined in Table 6. Complete conversion of the $C_3/C_4$ olefins was observed. The results of the testing are presented in Table 6. Sec-Butyl Benzene and cumene were formed in high selectivity with a smaller amount of di- and tri-alkyl benzenes than expected. Due to the fact that a mixture of olefins was used, the product did contain some di-alkyl benzene species containing both a $C_3$ and a $C_4$ chain in the product.

TABLE 6

Alkylation of Benzene with a 1:1 molar blend of propylene and trans-2-Butene

| Conditions | | |
|---|---|---|
| Time on Stream, (hrs.) | | 625 |
| Temperature, (deg. C.) | | 133 |
| Operating Pressure, (psig) | | 288 |
| Total Olefin + Benzene Feedrate, (g/Hr) | | 154 |
| | Feedstock | Product |
| trans-2-Butene, (wt. %) | 1.340 | <0.001* |
| Propylene, (wt. %) | 0.971 | <0.001* |
| Moles of propylene + trans-2-Butene, (moles/100 g) | 0.0478 | * |
| Benzene, (wt. %) | 97.475 | 94.059 |
| sec-Butyl Benzene, (wt. %) | <0.001* | 3.175 |
| Cumene, (wt. %) | <0.001* | 2.692 |
| 1,3-DIPB (wt. %) | <0.001* | 0.012 |
| 1,4-DIPB (wt. %) | <0.001* | 0.014 |
| 1,3,5-TIPB (wt. %) | <0.001* | 0.004 |
| 1,3-DSBB (wt. %) | <0.001* | 0.005 |
| 1,4-DSBB (wt. %) | <0.001* | 0.005 |
| 1,3,5-TSBB (wt. %) | <0.001* | <0.001* |
| Other di-alkyl benzenes | <0.001* | 0.031 |
| % Conversion of propylene and trans-2-Butene | | >99.9 |
| % Selectivity to Cumene | | 97.1 |
| % Selectivity to sec-Butyl Benzene | | 99.0 |
| Total moles of di- and tri-alkyl Benzenes produced/ 100 g of product | | 0.00041 |

*Not Detected by GC

EXAMPLE 6

Reaction of a 4:1 Molar Blend of Propylene and trans-2-Butene with Benzene

An olefin blend of 80% propylene and 20% trans-2-butene (on a molar basis) was reacted over the CP 786 catalyst at the conditions outlined in Table 7. Complete conversion of the $C_3/C_4$ olefins was observed. Sec-butyl benzene and cumene were formed in high selectivity with a smaller amount of di- and tri-alkyl benzenes produced than when a similar number of moles of only propylene were used (Example 2). The total amount of moles of di- and tri-alkyl benzenes produced per 100 g of product was 0.00074 moles. This was at least 38% less than the predicted amount (approximately 0.001 moles) based on interpolation from the amounts produced using the same number of moles of propylene or trans-2-butene only (see FIG. 1).

TABLE 7

Alkylation of Benzene with a 4:1 molar blend of propylene and trans-2-Butene

| Conditions | | |
|---|---|---|
| Time on Stream, (hrs.) | | 668 |
| Temperature, (deg. C.) | | 133 |
| Operating Pressure, (psig) | | 288 |
| Total Olefin + Benzene Feedrate, (g/Hr) | | 152 |
| | Feedstock | Product |
| trans-2-Butene, (wt. %) | 0.536 | <0.001* |
| Propylene, (wt. %) | 1.609 | <0.001* |
| Moles of propylene + trans-2-Butene, (moles/100 g) | 0.0478 | * |
| % Conversion of propylene and trans-2-Butene | | >99.9 |
| Total moles of di- and tri-alkyl Benzenes produced/ 100 g of product | | 0.00074 |

*Not Detected by GC

EXAMPLE 7

Reaction of a 1:4 Molar Blend of Propylene and trans-2-Butene with Benzene

An olefin blend of 20% propylene and 80% trans-2-Butene (on a molar basis) was reacted over the CP 786 catalyst at the conditions outlined in Table 8. Complete conversion of the $C_3/C_4$ olefins was again observed. Sec-butyl benzene and cumene were formed in high selectivity with a smaller amount of di- and tri-alkyl benzenes produced than when a similar number of moles of only propylene were used (Example 2). The total amount of moles of di- and tri-alkyl benzenes produced per 100 g of product was 0.00026 moles. This was at least 53% less than the predicted amount (0.0004 moles) based on interpolation from the amounts produced using the same number of moles of propylene or trans-2-butene only (see FIG. 1).

TABLE 8

Alkylation of Benzene with a 1:4 molar blend of propylene and trans-2-Butene

| Conditions | | |
|---|---|---|
| Time on Stream, (hrs.) | | 699 |
| Temperature, (deg. C.) | | 133 |
| Operating Pressure, (psig) | | 288 |
| Total Olefin + Benzene Feedrate, (g/Hr) | | 154 |
| | Feedstock | Product |
| trans-2-Butene, (wt. %) | 2.146 | 0.001* |
| Propylene, (wt. %) | 0.402 | <0.001* |
| Moles of propylene + trans-2-Butene, (moles/100 g) | 0.0478 | * |
| % Conversion of propylene and trans-2-Butene | | >99.9 |
| Total moles of di- and tri-alkyl Benzenes produced/ 100 g of product | | 0.00026 |

*Not Detected by GC

The results of Examples 1-7 indicate that reduced amounts of di- and tri-alkyl benzenes are produced when one or more linear butene(s) are added to propylene during the alkylation of benzene using the beta zeolite catalyst. This is clearly seen in FIG. 1.

EXAMPLE 8

Reaction of trans-2-Butene with Benzene when 0.11 wt % Isobutylene is Added

The feedstock used in Example 3 (benzene and trans-2-butene) was spiked with 0.11 wt. % isobutylene in order to examine the impact of isobutylene on the alkylation of benzene. The spiked mixture was reacted over the CP 786 catalyst at the conditions outlined in Table 9. Complete conversion of the linear butene was observed although the isobutylene was not completely converted. Sec-butyl benzene was formed in slightly lower selectivity than in Example 3 along with the observed production of some tert-butylbenzene. Since tert-butyl benzene and sec-butyl benzene have boiling points close to each other, they can be difficult to separate by simple distillation. It is therefore advisable to minimize the amount of isobutylene used when alkylating benzene with one or more linear butene(s) in order to simplify the purification of sec-butyl benzene.

The total amount of moles of di-alkyl benzenes produced per 100 g of product was 0.0006 moles. No tri-alkyl benzenes were observed in the product. This was similar to that observed in Example 3. However, a higher amount of octenes were observed in the product when isobutylene was used. These octenes were mainly branched and were likely produced via the dimerization of isobutylene.

TABLE 9

Alkylation of Benzene with trans-2-Butene (spiked with 0.11 wt % Isobutylene)

| Conditions | | |
|---|---|---|
| Time on Stream, (hrs.) | | 186 |
| Temperature, (deg. C.) | | 132 |
| Operating Pressure, (psig) | | 290 |
| Total Olefin + Benzene Feedrate, (g/Hr) | | 156 |
| | Feedstock | Product |
| Isobutylene | 0.110 | 0.013 |
| trans-2-Butene, (wt. %) | 1.608 | <0.001* |
| trans-2-Butene, (moles/100 g) | 0.028 | * |
| Benzene, (wt. %) | 97.941 | 95.732 |

TABLE 9-continued

Alkylation of Benzene with trans-2-Butene
(spiked with 0.11 wt % Isobutylene)

| | | |
|---|---|---|
| sec-Butyl Benzene, (wt. %) | <0.001* | 3.738 |
| % Conversion of Isobutylene | | 88.2 |
| % Conversion of trans-2-Butene | | >99.9 |
| % Selectivity to sec-Butyl Benzene | | 99.4 |
| Total moles of di- and tri-alkyl Benzenes produced/ 100 g of product | | 0.00006 |

*Not Detected by GC

General Comments

The alkylation tests were conducted in a laboratory scale, fixed bed reactor operating under liquid phase conditions. The reactants were carefully mixed and then passed over a CP786 zeolite beta catalyst, manufactured by Zeolyst International. The testing conditions were similar to the conditions used in modern cumene plants. The results showed that sec-butylbenzene could be produced at a selectivity of up to 99.5% while cumene was produced with a selectivity of 98.5% or less when the linear butene(s)/propylene feeds were used at a concentrations of between 1 and 4 mole percent in the benzene rich feed. The quantity of dialkylbenzenes and trialkylbenzenes produced with the linear butene(s)/propylene feeds was found to be around 30% lower than predicted based on the concentration of alkylating agent and the molar blend of propylene and linear butene(s). The difference in the amount of dialkylbenzenes and the trialkylbenzenes produced accounted for the main differences in the observed selectivities. The higher selectivity to sec-butylbenzene observed may permit a reduction in the size of the transalkylator needed.

In other tests, the impact of isobutylene in the linear butene feedstock used was investigated. As isobutylene was added to the linear butene feedstock, the amount of tert-butylbenzene produced increased. At the same time, octene dimers in the effluent began to be observed. These experiments suggest that isobutylene needs to be maintained at a very low level in the feed in order to mitigate the formation of tert-butylbenzene which is difficult to separate by simple distillation. Fortunately, the temperature at which the alkylation reaction is performed is low enough to minimize skeletal isomerization of the linear butene(s) into isobutylene.

The operational stability of the zeolite beta catalyst also was examined. While operating at the conditions used in testing, the catalyst was operated for over 2,500 hours without noticeable deactivation.

Persons of ordinary skill in the art will recognize that many modifications may be made to the foregoing without departing from the spirit and scope thereof. The embodiment described herein is meant to be illustrative only and should not be taken as limiting the invention, which is defined in the following claims.

We claim:

1. A method for increasing selectivity of aromatic alkylation to monoalkylation comprising:
   providing a feedstream consisting essentially of a concentration of alkylating agent and a stoichiometric excess of benzene, said alkylating agent consisting essentially of a molar blend of propylene and one or more linear butene(s); and,
   contacting said feedstream with a catalytically effective amount of zeolite beta under alkylation reaction conditions which increase selectivity of the alkylation to monoalkylation compared to predicted selectivity to monoalkylation based on the concentration of the alkylating agent and on the molar blend of propylene and one or more linear butene(s).

2. The method of claim 1 further comprising:
   providing said concentration of from about 1 to about 4 mole percent alkylating agent, said alkylating agent comprising about 200 ppm or less isobutylene;
   providing from about a 1:4 to about a 4:1 molar blend of propylene to one or more linear butene(s); and,
   maintaining a reaction temperature which minimizes skeletal isomerization of the one or more linear butene(s) to isobutylene.

3. The method of claim 1 producing actual total moles of di- and tri-alkylated aromatic compounds at molar ratios of propylene:linear butene(s) of from about 1:4 to about 4:1, said actual total moles being at least 10% less than projected total moles of di- and tri-alkyl benzenes per 100 g product predicted based on the concentration of alkylating agent and the molar blend of propylene and one or more linear butene(s).

4. The method of claim 1 further comprising providing the one or more linear butene(s) comprising 100 ppm or less isobutylene.

5. The method of claim 1 wherein said conditions comprise:
   a reaction temperature of from about 100° C. to about 150° C.; and,
   a reaction pressure of from about 250 psig to about 350 psig.

6. The method of claim 3 wherein said conditions comprise:
   a reaction temperature of from about 110° C. to about 145° C.; and,
   a reaction pressure of from about 270 psig to about 325 psig;
   a total liquid feed rate of about 40 g/hr to about 200 g/hr for about 25 g total weight of catalyst, based on combined weight of zeolite beta catalyst powder and binder.

7. The method of claim 5, said conditions producing:
   conversion of 99% or more of said concentration of one or more linear butene(s); and,
   conversion of 99% or more of said concentration of propylene.

8. The method of claim 6, said conditions producing:
   conversion of 99% or more of said concentration of one or more linear butene(s); and,
   conversion of 99% or more of said concentration of propylene.

9. The method of claim 6, said conditions producing
   conversion of 99.9% or more of said concentration of one or more linear butene(s); and,
   conversion of 99.9% or more of said concentration of propylene.

10. The method of claim 1 further comprising producing selectivity to sec-butylbenzene of about 98% or more; and,
   selectivity to cumene of about 95% or more.

11. The method of claim 1 further comprising producing selectivity to sec-butylbenzene of about 99% or more; and,
   selectivity to cumene of about 97% or more.

12. The method of claim 1 further comprising producing selectivity to sec-butylbenzene of about 99.5% or more; and,
   selectivity to cumene of about 97% or more.

13. A method for increasing selectivity of aromatic alkylation to monoalkylation comprising:

providing a feedstream consisting essentially of a concentration of alkylating agent and a stoichiometric excess of benzene, said alkylating agent consisting essentially of a molar blend of propylene and one or more linear butene(s); and, contacting said feedstream with a catalytically effective amount of zeolite beta under alkylation reaction conditions producing actual total moles of di- and tri-alkylated aromatic compounds per 100 g product at molar ratios of propylene:linear butene(s) of from about 1:4 to about 4:1, said actual total moles being at least 10% less than projected total moles of di- and tri-alkyl benzenes per 100 g product predicted based on the concentration of alkylating agent and the molar blend.

14. The method of claim 13 producing actual total moles of di- and tri-alkylated aromatic compounds per 100 g product at molar ratios of propylene:linear butene(s) of from about 1:4 to about 4:1, said actual total moles being at least 30% less than projected total moles of di- and tri-alkyl benzenes per 100 g product predicted based on the concentration of alkylating agent and the molar blend.

15. The method of claim 13 further comprising:

providing said concentration comprising from about 1 to about 4 mole percent alkylating agent, said alkylating agent comprising about 200 ppm or less isobutylene;

providing from about a 1:4 to about a 4:1 molar blend of propylene to one or more linear butene(s);

maintaining a reaction temperature of from about 100° C. to about 150° C.; and, maintaining a reaction pressure of from about 250 psig to about 350 psig.

16. The method of claim 14 further comprising:

providing said concentration comprising from about 1 to about 4 mole percent alkylating agent, said alkylating agent comprising about 200 ppm or less isobutylene;

providing from about a 1:4 to about a 4:1 molar blend of propylene to one or more linear butene(s);

maintaining a reaction temperature of from about 100° C. to about 150° C.; and, maintaining a reaction pressure of from about 250 psig to about 350 psig.

17. A method for increasing selectivity of aromatic alkylation to monoalkylation comprising:

providing a feedstream consisting essentially of alkylating agent and a stoichiometric excess of benzene, said alkylating agent consisting essentially of a molar blend of propylene and one or more linear butene(s); and, contacting said feedstream with a catalytically effective amount of zeolite beta under alkylation reaction conditions which increase selectivity of the alkylation to monoalkylation compared to predicted selectivity to monoalkylation based on the concentration of the alkylating agent and on the molar blend of propylene and one or more linear butene(s), producing an alkylator product stream;

removing benzene from said alkylator product stream, producing a benzene-depleted stream; and recovering said monoalkylated benzene from said benzene-depleted stream.

18. The method of claim 17 producing actual total moles of di- and tri-alkylated aromatic compounds per 100 g product at molar ratios of propylene:linear butene(s) of from about 1:4 to about 4:1, said actual total moles being at least 20% less than projected total moles of di- and tri-alkyl benzenes per 100 g product predicted based on the concentration of alkylating agent and the molar blend.

19. The method of claim 17 producing actual total moles of di- and tri-alkylated aromatic compounds per 100 g product at molar ratios of propylene:linear butene(s) of from about 1:4 to about 4:1, said actual total moles being at least 30% less than projected total moles of di- and tri-alkyl benzenes per 100 g product predicted based on the concentration of alkylating agent and the molar blend.

20. The method of claim 17 further comprising removing light ends and water from said alkylator product, producing a light ends column stream;

recycling said benzene removed from said alkylator product stream to said alkylator.

21. The method of claim 20 where said recovering said monoalkylated benzene produces a remainder, said method further comprising separating a dialkyl benzene stream from said remainder.

22. The method of claim 21 further comprising contacting said remainder with a transalkylation catalyst under conditions effective to produce supplemental monoalkylated benzene;

recovering said supplemental monoalkylated benzene.

23. The method of claim 22 further comprising removing light ends and water from said alkylator product, producing a light ends column stream.

24. The method of claim 23 further comprising recycling said benzene removed from said alkylator product stream to said alkylator.

25. The method of claim 17 further comprising:

providing said concentration comprising from about 1 to about 4 mole percent alkylating agent, said alkylating agent comprising about 200 ppm or less isobutylene;

providing from about a 1:4 to about a 4:1 molar blend of propylene to one or more linear butene(s);

maintaining a reaction temperature of from about 100° C. to about 150° C.; and, maintaining a reaction pressure of from about 250 psig to about 350 psig.

26. The method of claim 24 further comprising:

providing said concentration comprising from about 1 to about 4 mole percent alkylating agent, said alkylating agent comprising about 200 ppm or less isobutylene;

providing from about a 1:4 to about a 4:1 molar blend of propylene to one or more linear butene(s);

maintaining a reaction temperature of from about 100° C. to about 150° C.; and, maintaining a reaction pressure of from about 250 psig to about 350 psig.

27. The method of claim 17 said conditions producing:

conversion of 99% or more of said concentration of one or more linear butene(s); and, conversion of 99% or more of said concentration of propylene.

28. The method of claim 26, said conditions producing conversion of 99.9% or more of said concentration of one or more linear butene(s); and, conversion of 99.9% or more of said concentration of propylene.

29. The method of claim 22 further comprising providing said transalkylation catalyst selected from the group consisting of zeolite Y and solid phosphoric acid.

30. The method of claim 28 further comprising providing said transalkylation catalyst selected from the group consisting of zeolite Y and solid phosphoric acid.

31. The method of claim 17 further comprising producing selectivity to sec-butylbenzene of about 98% or more; and, selectivity to cumene of about 95% or more.

32. The method of claim 17 further comprising producing selectivity to sec-butylbenzene of about 99% or more; and, selectivity to cumene of about 97% or more.

33. The method of claim 24 further comprising producing selectivity to sec-butylbenzene of about 99.5% or more; and, selectivity to cumene of about 97% or more.

* * * * *